United States Patent [19]

Heyman

[11] Patent Number: 4,881,552
[45] Date of Patent: Nov. 21, 1989

[54] TOOTH STABILITY MONITOR

[75] Inventor: Joseph S. Heyman, Williamsburg, Va.

[73] Assignee: Measurement Resources Inc., Newport News, Va.

[21] Appl. No.: 146,288

[22] Filed: Jan. 20, 1988

[51] Int. Cl.⁴ ............................................... A61B 5/10
[52] U.S. Cl. .................................... 128/774; 128/776; 3/513; 3/72; 3/215
[58] Field of Search ............... 128/776, 774, 739, 649, 128/65 L; 73/82, 83; 433/32, 72, 215; 33/513, 514

[56] References Cited

U.S. PATENT DOCUMENTS

| | | | |
|---|---|---|---|
| 3,094,115 | 6/1963 | Polin | 433/72 |
| 3,875,420 | 4/1975 | Ryden et al. | 433/32 |
| 3,943,913 | 3/1976 | Johnson | 433/32 |
| 4,058,115 | 11/1977 | Forst | 128/776 |
| 4,192,321 | 3/1980 | Korber et al. | 128/776 |
| 4,197,641 | 4/1980 | Paulke et al. | 433/32 |
| 4,470,810 | 9/1984 | Bourdeau et al. | 433/72 |
| 4,499,906 | 2/1985 | Wohlgemuth et al. | 128/776 |
| 4,665,621 | 5/1987 | Ackerman et al. | 33/513 |
| 4,764,114 | 8/1988 | Jeffcoat et al. | 128/776 X |

FOREIGN PATENT DOCUMENTS

| | | | |
|---|---|---|---|
| 2733081 | 2/1979 | France | 128/776 |
| 205214 | 9/1966 | U.S.S.R. | 128/776 |

Primary Examiner—Max Hindenburg
Assistant Examiner—J. P. Lacyk
Attorney, Agent, or Firm—William H. King

[57] ABSTRACT

A tooth stability monitor for assessing the rigidity of a tooth. A tooth probe 11 is provided for sinusoidally moving the tooth at a constant small amplitude. A displacement sensor 13 measures the resulting displacement of the tooth and a force sensor 14 measures the resulting force applied to the tooth. Feedback electronics 15 receives the two measurements and calculates the tooth modulus.

6 Claims, 1 Drawing Sheet

TOOTH STABILITY MONITOR

BACKGROUND OF THE INVENTION

The invention relates to an instrument for assessing the rigidity or stiffness of any structure and more specifically concerns a tooth stability monitor for assessing the rigidity of a tooth in the jaw of a patient as a monitor of periodontal disease.

In the past the usual practice to determine the stability of a tooth is based on the "feel" of the tooth during hand manipulation. This practice is subjective and prone to error.

The prior art also discloses in U.S. Pat. No. 3,943,913 apparatus and method for determining tooth mobility. In this disclosure a probe is fixed inside the patient's mouth such that the probe is touching the tooth under examination. Then the tooth is pushed and pulled manually by means of a manipulating tool and the resulting movement of the tooth is sensed by the probe. The disadvantages of this device are that it is time-consuming to fix the probe in the patient's mouth and it is prone to error because there is no way to determine the force applied to the tooth except by the feel of the operator and is therefore prone to error.

In addition, the prior art discloses in U.S. Pat. No. 4,470,810 an instrument that applies a single impulse to a tooth and then the resulting rate of movement of the tooth is measured. The disadvantages of this device are that since it is a single impulse device, frequency and amplitude effects cannot be measured and it cannot have pull, and push and pull modes of operation.

It is an object of this invention to provide an instrument for assessing the rigidity or stiffness of any structure.

Another object of this invention is to provide a simple, easy to use tooth stability monitor.

A further object of this invention is to provide a tooth stability monitor that does not depend on the feel of the operator.

Still another object of this invention is to provide a tooth stability monitor that does not require time-consuming preparations prior to the use of the monitor.

A still further object of this invention is to provide a tooth stability monitor that can measure the effects at different frequencies and amplitudes of the movement of a tooth.

Yet another object of this invention is to provide a tooth stability monitor that can have either push, pull, or push/pull modes of operation.

Other objects and advantages of this invention will become apparent hereinafter in the specification and drawings.

SUMMARY OF THE INVENTION

The invention is a tooth probe having a tip which is placed against the tooth that is to be tested for stability. The tip is driven in a sinusoidal fashion at various frequencies at a constant, but small amplitude by a constant amplitude device. A displacement sensor measures the tip motion relative to the probe body and provides that information to feedback electronics. Similarly, a force sensor measures the stress or force delivered to the tip and provides that information to the electronics. The feedback electronics maintains the constant amplitude vibration while calculating the effective tooth modulus. The modulus is determined at several frequencies and as a function of amplitude to determine the nonlinearity of the tooth modulus. A probe body accelerometer provides a high accuracy correction to remove the effect of the relatively small probe body vibrations that occur as a reaction to the driver force.

DETAILED DESCRIPTION OF THE INVENTION

The engineering assessment of material stiffness is achieved through a measurement of modulus or elastic constants. Such measurements require that a force ($\sigma$) be applied to the material in question and resulting strain ($\epsilon$) (displacement/initial length) determined. Using the following equation: $\sigma = \epsilon \mathrm{x} M$ one can determine M, where M is the modulus in question. Note that it is necessary to measure both $\sigma$ and $\epsilon$ simultaneously.

Figure 1:
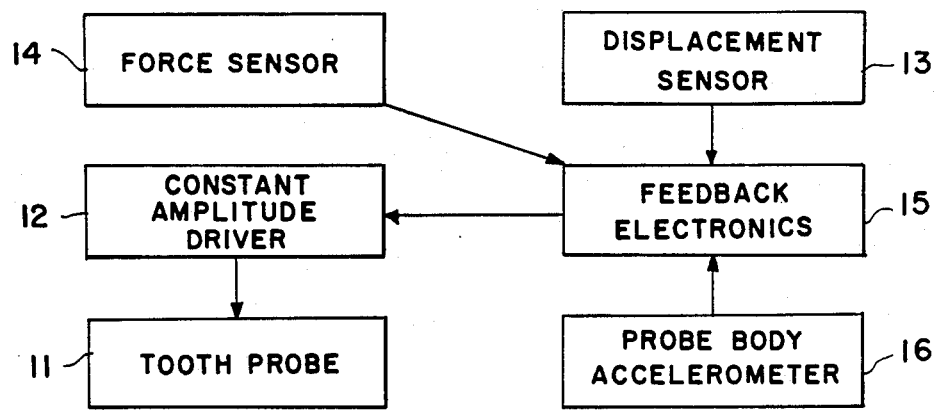
FIG. 1 is a block diagram of the invention.
Figure 2:
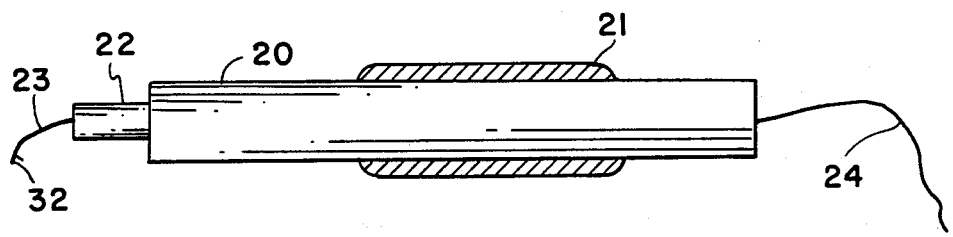
FIG. 2 is a drawing of the tooth probe shown in FIG. 1.
Figure 3:
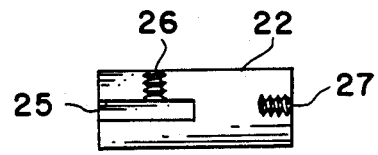
FIG. 3 is a drawing of the probe mount shown in FIG. 2.
Figure 4:
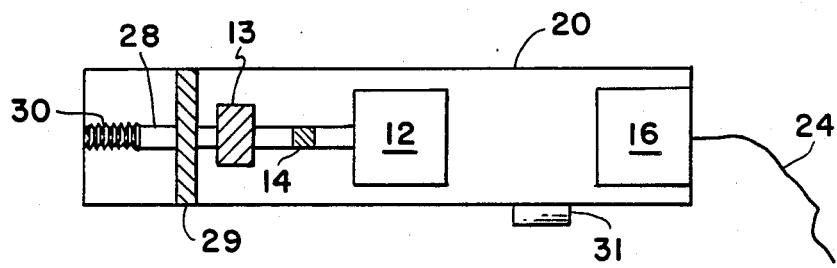
FIG. 4 is a drawing of the probe body shown in FIG. 2.

Turning now to the embodiment of the invention selected for illustration in the drawing the number 11 in FIG. 1 designates a tooth probe which is described in more detail in FIGS. 2, 3, and 4. The tip of tooth probe 11 is placed against the tooth under investigation. A constant amplitude driver 12 drives in a sinusoidal fashion the tip relative to the tooth probe body thereby imparting movement to the tooth. The movement amplitude produced by driver 12 is small constant and in the direction parallel to the longitudinal axis of the probe body. A displacement sensor 13 measures the resulting displacement ($\epsilon$) of the tip relative to the body of the tooth probe and a force sensor 14 measures the resulting force ($\sigma$) applied to the tooth by the tip. Both of these measured signals are applied to a feedback electronics 15. Feedback electronics 15 provides two functions: it maintains the constant amplitude vibrations applied to the tooth by driver 12 and it calculates in accordance with the equation $\sigma = \mathrm{x} M$, the effective tooth modulus M using the measured signals from displacement sensor 13 and force sensor 14. The device can operate at one frequency and amplitude or can perform the measurement at several frequencies and amplitudes to assess the stability of the tooth. By determining M as a function of amplitude, the nonlinearity of M is determined for a complete characterization of the tooth stability. Circuitry for performing the functions of feedback electronics 15 will be obvious to one skilled in the art and will therefore not be disclosed in detail in this specification.

The tooth probe 11, as shown in FIG. 2, includes a cylindrical probe body 20 with a handle 21 for the user. A probe mount 22 is slidably attached to probe body 20 so that it will slide back and forth in probe body 20, but will not rotate. A tooth probe tip 23 similar to a common tooth probe tip is inserted into and held by probe mount 22. Tooth probe tip 23 includes a tab 32 which can be placed over a tooth for a push/pull operation, placed against the front of the tooth for a push operation or placed against the back of the tooth for a pull operation. A wire or group of wires 24 connects the tooth probe to the feedback electronics 15.

The probe mount 22, as shown in FIG. 3, includes a hole 25 into which a tooth probe tip 23 is inserted (a different tip is used for each patient) and is held in place by a set screw 26. Female threads 27 are located on the opposite end of probe mount 22 for the reception of a shaft having male threads included with probe body 20.

The probe body 20, as shown in FIG. 4, includes a shaft 28 rotatably mounted inside the probe body by means of a suitable mounting means 29. Shaft 28 has male threads 30 on its end that mate with the female threads 27 in probe mount 22. Shaft 28 is rotated by the constant amplitude driver 12. Shaft 28 extends through the displacement sensor 13 which is a common linear variable differential transformer (LVDT). The force snesor 14 is a strain gauge that is an integral part of the threaded shaft 28. Constant amplitude driver 12 is electromagnetic and similar to a voice coil design such as is used to move pick-up heads in disk drives and speaker cones taking advantage of high field samarian cobalt magnets for weight reduction. The probe body accelerometer 16 is attached to probe body 20 and connected by one of the wires 24 to the feedback electronics 15. An external adjustment 31 is used for selecting constant displacement amplitude and frequency for constant amplitude driver 12. The displacement sensor 13 is necessary to ensure that the system is operating at the constant displacement amplitude selected by adjustment 31. Constant amplitude driver 12, displacement sensor 13, force sensor 14 and external adjustment 31 are all connected (not shown in FIG. 4) through wires 24 to the feedback electronics 15.

The advantages of this invention are that it provides a simple, easy to use tooth stability monitor that is accurate, easy to use, does not require time-consuming preparations prior to its use and does not depend on the feel of the operator.

Numerous modifications of the disclosed embodiment of this invention can be made without altering the scope of the invention. For example, the displacement sensor can be any sensor for displacement such as an optical fiber and light source. All the sensors can be modified to take advantage of optimum properties. The application of the device is broader than dental applications and can be used to assess the rigidity or stiffness of any structure. The invention can also measure the phase angle between the internal displacement sensor and the force sensor as a function of both amplitude as well as frequency to determine the elastic/anelastic properties of of the resisting body. Measurements of the effective modulus as a function of tip amplitude can also be used to determine the nonlinear characteristics of the structure (higher order elastic constants) which are important to provide a more complete analysis of the joint.

What is claimed is:

1. A tooth stability monitor comprising:
    means for sinusoidally moving the tooth under investigation at a small constant amplitude comprising a hand held tooth probe including a probe tip mounted in a probe mount for making contact with the tooth, a hand held probe body, and means for sinusoidally moving said probe mount relative to said hand held probe body;
    means for generating a first electrical signal representing the resulting displacement of the tooth;
    means for generating a second electrical signal representing the force applied to said tooth to produce the movement of the tooth;
    means for generating a third electrical signal proportional to vibrations of said hand held probe body; and
    means receiving said first, second and third electrical signals for modifying said first and second electrical signals to remove the effects of the hand held probe body vibrations, and for computing the tooth modulus using the modified first and second electrical signals.

2. A tooth stability monitor according to claim 1 wherein said means for sinusoidally moving the tooth under investigation includes means for varying the amplitude and frequency of the movement whereby nonlinear modulus and phase angle can be determined.

3. A tooth stability monitor according to claim 1 wherein said means for sinusoidally moving said probe mount relative to said probe body includes a shaft mounted for movement inside said probe body and a constant amplitude driver for moving said shaft relative to said probe body.

4. A tooth stability monitor according to claim 3 wherein said shaft is attached to said probe mount for moving said probe mount and said tip relative to said probe body.

5. A tooth stability monitor according to claim 4 wherein said means for generating said first electrical signal is a linear variable differential transformer inside said probe body for generating a signal proportional to the movement of said shaft.

6. A tooth stability monitor according to claim 4 wherein said means for generating a second electrical signal is a transducer integral with said shaft for generating a signal proportional to the force exerted by said shaft through the probe mount tip to said tooth.

* * * * *